United States Patent
Plat et al.

(10) Patent No.: US 8,324,187 B2
(45) Date of Patent: Dec. 4, 2012

(54) STABILIZED FORMULATIONS OF PHOSPHATIDYLSERINE

(75) Inventors: Dorit Plat, Shimshit (IL); Avidor Shulman, Kiryat Tivon (IL); Gai Ben Dror, Moshav Ofer (IL); Neta Scheinman, Haifa (IL); Yoni Twito, Geva Carmel (IL); Rassan Zuabi, Kfar Neen (IL)

(73) Assignee: Enzymotec Ltd., Migdal Haemeq (IL)

( * ) Notice: Subject to any disclaimer, the term of this patent is extended or adjusted under 35 U.S.C. 154(b) by 771 days.

(21) Appl. No.: 10/572,782

(22) PCT Filed: Sep. 26, 2004

(86) PCT No.: PCT/IL2004/000895
§ 371 (c)(1),
(2), (4) Date: Nov. 8, 2006

(87) PCT Pub. No.: WO2005/027822
PCT Pub. Date: Mar. 31, 2005

(65) Prior Publication Data
US 2007/0160659 A1 Jul. 12, 2007

(30) Foreign Application Priority Data
Sep. 25, 2003 (IL) .......................................... 158139

(51) Int. Cl.
*A61K 36/48* (2006.01)
*A61K 47/00* (2006.01)
*A61K 9/48* (2006.01)
*A61K 9/64* (2006.01)
*A61K 31/685* (2006.01)
*A61K 31/66* (2006.01)

(52) U.S. Cl. ............ 514/75; 514/78; 424/757; 424/439; 424/451; 424/456

(58) Field of Classification Search .................. 424/757, 424/439, 451, 456; 514/75, 78
See application file for complete search history.

(56) References Cited

U.S. PATENT DOCUMENTS

| | | | |
|---|---|---|---|
| 3,357,918 A | | 12/1967 | Davis |
| 5,015,483 A | * | 5/1991 | Haynes et al. .................. 426/73 |
| 5,700,668 A | | 12/1997 | De Ferra et al. |
| 6,514,973 B1 | * | 2/2003 | Buchholz et al. ............. 514/249 |
| 6,645,742 B2 | | 11/2003 | De Ferra et al. |
| 2004/0120985 A1 | * | 6/2004 | Geiss ............................. 424/439 |
| 2008/0085319 A1 | * | 4/2008 | Dror et al. ..................... 424/523 |
| 2008/0085320 A1 | * | 4/2008 | Dror et al. ..................... 424/523 |
| 2009/0011075 A1 | * | 1/2009 | Shulman et al. .................. 426/2 |
| 2009/0074857 A1 | * | 3/2009 | Dror et al. ..................... 424/456 |

FOREIGN PATENT DOCUMENTS

| | | |
|---|---|---|
| DE | 199 17 249 A1 | 9/2000 |
| EP | 922707 A1 * | 6/1999 |
| EP | 1213294 A1 | 6/2002 |
| JP | 2001122884 A | 5/2001 |
| JP | 2001354680 A | 12/2001 |
| JP | 2002241385 A | 8/2002 |
| JP | 2006-527572 | 6/2011 |
| WO | WO 00/56869 | 9/2000 |
| WO | WO 0182902 A1 * | 11/2001 |
| WO | WO 0184961 A2 * | 11/2001 |
| WO | WO 03/088949 | 10/2003 |

OTHER PUBLICATIONS

The Merck Manuals, http://www.merck.com/mmhe/sec06/ch083/ch083c.html?qt=memory%20loss&alt=sh, 2008, obtained on Mar. 20, 2009.*
Jorissen et al., Nutritional Neuroscience, 2002, 5(5), 337-343.*
Douglas Laboratories, 1999, Product Data Scheet, obtained online at: https://www.emersonecologics.com/Content/PDF/ProductSheets/PHS.pdf on Mar. 9, 2010.*
International Search Report PCT/IL2004/000895.
International Preliminary Report on Patentability PCT/IL2004/000895.
Wu Wutong, Biochemistry 4th Edition, p. 149 (in chinese).
Lekh Raj Juneja et al "Conversion of phosphatidylcholine to phosphatidylserine by various phospholipases D in the presence of L- or D-serine", Biochimica et Biophysica Acta, 1003 (1987) 277-283, pp. 277-283.
Notification of Reason for Refusal dated Jun. 14, 2011 for Patent Application No. JP 2006-527572.
Yamane: "Enzyme engineering for lipids", proc. Sat. Forum, sustainable agricultural system in Asia, Nagoya: Jun. (2002), pp. 61-68, XP 002562623.

* cited by examiner

*Primary Examiner* — Abigail Fisher
(74) *Attorney, Agent, or Firm* — Martin Fleit; Paul D. Bianco; Fleit Gibbons Gutman Bongini & Bianco PL

(57) ABSTRACT

Disclosed are stable PS preparations, in powder, liquid and dispersion forms, as well as methods of producing thereof. Most importantly, the stable PS preparations are particularly devoid of residual phospholipase D activity, and the methods of eliminating such activity are also described herein. Lastly, uses of these PS preparations in nutraceuticals or as active agents of pharmaceutical compositions are also provided herein.

12 Claims, No Drawings

STABILIZED FORMULATIONS OF PHOSPHATIDYLSERINE

FIELD OF THE INVENTION

The invention relates to stabilized phosphatidylserine preparations and to methods for preparing them. The stabilized phosphatidylserine preparations of the invention may be in the form of powder, liquid or dispersion. The phosphatidylserine preparations can be used as nutraceuticals or nutraceutical additives to functional foods or pharmaceutical compositions.

BACKGROUND OF THE INVENTION

All publications mentioned throughout this application are fully incorporated herein by reference, including all references cited therein.

Phosphatidylserine (PS), a phospholipid nutrient, is active in cell membranes and is the major acidic phospholipid component in the membrane of brain cells. PS plays a crucial role in many membrane-associated nerve cell processes. The main purpose of PS is to help maintain proper membrane fluidity, which has major implications on most membrane functions.

PS has been the subject of numerous human clinical trials of memory loss, mood, cognitive performance and learning ability. Many of the studies show that PS can be helpful for those with age-related memory impairment. Moreover, PS can even help to optimize cognition in those with no cognitive impairment.

Dietary PS is efficiently and rapidly absorbed in the intestine, taken up into the blood, and readily crosses the blood-brain barrier to reach the nerve cells in the brain.

PS can be extracted from bovine brain, from plants or it can be produced from soybean lecithin using biocatalysis. By using the transphosphatidylation reaction with phospholipases D (PLDs), the head group of phospholipids can be modified easily. Thus, phosphatidylserine can be produced from phosphatidylcholine or any other phospholipid mixture with serine through PLD catalysis.

Currently, PS is manufactured and marketed in powder and fluid forms, at different concentrations, ranging from 10% to 90%. The fluid form of the PS commonly consists of a clear and transparent solution of phosphatidylserine, usually in oily media of medium-chain triglycerides (MCT) or soy triglycerides. This form is commonly used for dietary supplements in the form of softgel capsules. PS supplements fall within the category of nutraceuticals, which are defined as any substance that is a food, or part of a food and provides medical and/or health benefits, including the prevention and treatment of disease. In the broad definition, both dietary supplements and functional foods are considered nutraceuticals.

One of the main difficulties in phosphatidylserine preparations, especially in liquid form, is its low stability due to rapid decomposition. The exact cause of this decomposition is not fully understood. There are many hypotheses regarding the cause of this phenomenon, although most are not scientifically established or proved. The common belief is that decomposition is caused mainly by residual biocatalytic activity and/or side-reactions with water or glycerol as well as other alcohol moieties. These reactions can be especially important when the PS preparation is fluid, and it is encapsulated in softgel capsules. Softgel encapsulation usually results in the migration and subsequent incorporation of low levels of water and/or glycerol into the capsule content.

PS preparations, and especially fluid preparations, in which PLD residual biocatalytic activity is present may be susceptible to PS biocatalytic degradation by transphosphatidylation, which removes the serine head group, resulting in loss of the PS active ingredient. This transphosphatidylation activity can result in hydrolysis utilizing water found in the fluid PS preparation itself or the fluid preparation following encapsulation. Hydrolysis will lead to the formation of phosphatidic acid (PA). In case the transphosphatidylation utilizes glycerol or other alcohol moieties found in the fluid PS preparation itself or the fluid preparation following encapsulation, this may lead to the replacement of the serine head group with other alcohols, yielding phosphatidylglycerol (PG) or other corresponding phospholipid derivatives.

Other degradation routes are also possible. These include chemical degradation, like for example decarboxylation of the serine carboxylic group, yielding products such as phosphatidylethanolamine (PE) or other derivatives. Lipid peroxidation may also play a role in PS degradation. PS can be degraded by full or partial hydrolysis of the phospholipid fatty acids, yielding de-acylated PS (GPS) or lyso-PS (LPS), correspondingly. In case of PS phosphate removal, either enzymatically by enzymes with phospholipase C (PLC)-like activity or chemically, diglycerides can be created, also resulting in reduction of the PS active ingredient.

One way to overcome degradation has been proposed in WO 03/088949, wherein the phospholipid is embedded in a hard or paste-like matrix.

Besides what has been suggested above, other degradation pathways are plausible and might be responsible to the apparent degradation of PS in commercial preparations.

It is therefore an object of the present invention to provide stabilized PS preparations, as powders, liquids or dispersions.

It is a further object of the present invention to provide methods for the preparation of such stabilized PS preparations.

It is yet a further object of the present invention to provide the said stabilized preparations for use in common dietary supplements applications, and particularly in softgel capsules.

It is yet a further object of the present invention to provide the said stabilized preparations for use as stand-alone nutraceuticals or as additives to food articles or to pharmaceutical compositions.

These and other objects of the invention will become apparent as the description proceeds.

SUMMARY OF THE INVENTION

In order to overcome the problem of phosphatidylserine instability, the present inventors have developed and present herein a PS composition which is more stable. Uses and methods of producing such stable PS are also presented.

Thus, in a first aspect, the present invention provides a stable PS composition of matter comprising from about 1 to about 99% (w/w) phosphatidylserine.

In one embodiment of the composition of matter of the invention, said composition comprises from about 1 to about 99% (w/w) PS, preferably from about 2.5 to 80% (w/w), from about 1 to about 99% (w/w) other functional ingredients, preferably from about 5 to 90% (w/w), from about 1 to about 99% (w/w) phosphatidylcholine (PC), preferably from about 1 to 25% (w/w), preferably from about 1 to about 99% (w/w) phosphatidylethanolamine (PE), preferably from about 1 to 10% (w/w), from about 0.1 to about 99% (w/w) phosphatidylinositol (PI), preferably from about 0.5 to 10% (w/w), from about 1 to about 99% (w/w) Omega-3 source, preferably from about 10 to 90% (w/w), from about 1 to about 99% (w/w) Omega-6 source, preferably from about 10 to 90% (w/w), and/or from about 1 to about 99% (w/w) sterol or sterol esters, preferably from about 1 to 65% (w/w).

In addition, the composition of matter of the invention is characterized in that its content does not exceed 15% of phosphatidic acid (PA). Preferably, the PA content is below 10%, more preferably between 1 and 7%.

In another embodiment, the composition of matter of the invention is characterized in that no more than about 1 to about 5% of the phosphatidylserine is decomposed after a storage period of at least 6 months, preferably at least 12 months, more preferably at least 24 months.

In one particular embodiment of the present invention, the composition of matter is substantially devoid of phospholipase activity, particularly phospholipase D activity.

In another particular embodiment, the phosphatidylserine composition of matter of the present invention is in powder form.

In a further embodiment, the PS comprised in the composition of matter of the invention is in the form of a salt which is substantially soluble in organic solvents, particularly salts of monovalent ions, preferably sodium salt.

In an even further embodiment, the PS comprised in the composition of matter of the invention is in the form of a salt which is substantially non-soluble in organic solvents, particularly salts of divalent ions, preferably a calcium salt. Alternatively, it may also be a magnesium salt.

The composition of matter of the invention may further optionally comprise physiologically/pharmaceutically acceptable additives, such as free-flow agents, emulsifiers, stabilizers preservatives, colorants, anti-foaming agents and anti-caking agents, as well as diluents, excipients, and carriers.

In a yet further embodiment, the phosphatidylserine composition of matter of the invention is for use as a dietary supplement, nutraceutical food and/or as a drug additive.

In a second aspect, the present invention provides a stable liquid preparation of phosphatidylserine comprising the phosphatidylserine composition of matter of the invention wherein the PS is present in the form of a salt which is substantially soluble in organic solvents, dissolved in oil, preferably a medium-chain triglyceride. Preferably, said PS dissolved in oil is in the form of a sodium salt.

In one first embodiment, the liquid preparation of the invention comprises from about 1 to about 90% (w/w) of phosphatidylserine, preferably from about 2.5 to about 55% (w/w).

In another embodiment, the liquid phosphatidylserine preparation of the invention is characterized in that no more than about 1 to about 5% of the phosphatidylserine is decomposed after a storage period of at least 6 months, preferably at least 12 months, more preferably at least 24 months.

In a further embodiment, the liquid phosphatidylserine preparation of the invention further comprises additional bio-functional ingredients, preferably at least one of lecithin, phospholipids, vitamins, anti-oxidants, minerals, nutritional proteins or peptides, sterol and other derivatives, nutritional carbohydrates and their derivatives, amino acids, plant extracts, fermentation products, glyceride derivatives (mono- and di-glycerides), poly-unsaturated fatty acids, and Omega-3 and/or Omega-6 lipids.

In a yet further embodiment, the phosphatidylserine liquid preparation of the invention is for use as a dietary supplement, nutraceutical food and/or drug additive.

In a third aspect, the present invention provides a stable dispersion of phosphatidylserine comprising the stable phosphatidylserine composition of matter of the invention, wherein the PS is present in the form of a salt which is substantially non-soluble in organic solvents, dispersed in a liquid base. Preferably, said salt is a calcium salt. Thus, the stable dispersion of PS is a calcium salt of PS dispersed in a liquid base which is preferably lipid, more preferably an oil base. Alternatively, the stable dispersion of PS is a magnesium salt of PS dispersed in a liquid base which is preferably lipid, more preferably an oil base.

In one embodiment, a lipid base can be oil, esters of fatty acids, free fatty acids and other derivatives.

Preferably, said phosphatidylserine dispersion of the invention comprises from about 1 to about 70% (w/w) phosphatidylserine, most preferably from about 5 to 45% (w/w).

In one preferred embodiment of the phosphatidylserine dispersion of the invention, said oil base is a triglyceride base, particularly medium-chain triglycerides base or vegetable oil.

In another embodiment, the phosphatidylserine dispersion of the invention further comprises additional bio-functional ingredients, preferably at least one of lecithin, phospholipids, vitamins, anti-oxidants, minerals, nutritional proteins or peptides, sterol and other derivatives, nutritional carbohydrates and their derivatives, amino acids, plant extracts, fermentation products, glyceride derivatives (mono- and di-glycerides), poly-unsaturated fatty acids, and Omega-3 and/or Omega-6 lipids.

In a further embodiment, said phosphatidylserine dispersion of the invention is for use as a dietary supplement, nutraceutical food and/or drug additive.

In another aspect, the present invention provides a food article comprising PS in any one of the forms provided by the invention, i.e., as a phosphatidylserine composition of matter, as a PS liquid preparation or as a PS dispersion.

In one embodiment, said food article optionally further comprises at least one additional bio-functional ingredient, for example a bio-functional ingredient as described above.

In a following aspect, the present invention provides a pharmaceutical composition comprising as active agent PS in any one of the forms provided by the invention, i.e., as a phosphatidylserine composition of matter, as a PS liquid preparation or as a PS dispersion, and optionally further comprising at least one additional active agent and/or at least one pharmaceutically acceptable additive, diluent, carrier or excipient. The pharmaceutical composition of the invention may comprise additional pharmaceutically active agents.

In yet another aspect, the present invention provides a capsule containing PS in any one of the forms provided by the invention, i.e., as a phosphatidylserine composition of matter, as a PS liquid preparation or as a PS dispersion. Said capsule is preferably a soft gelatin capsule.

The present invention also provides the use of any of the PS preparations described in the invention, i.e., as a phosphatidylserine composition of matter, as a PS liquid preparation or as a PS dispersion, as an enhancer of cognitive performance and learning ability.

It is a subsequent aspect of the present invention to provide PS, in any one of the forms provided by the invention, i.e., as a phosphatidylserine composition of matter, as a PS liquid preparation or as a PS dispersion, for use in preventing memory loss, particularly age-related memory loss.

In a further aspect, the present invention provides a process for the preparation of a stable phosphatidylserine composition of matter, comprising the steps of:

(a) incubating an aqueous mixture of L-serine and optionally appropriate organic solvents with lecithin in the presence of an immobilized phospholipase for a suitable period of time to give phosphatidylserine;

(b) removing the upper layer which contains the phosphatidylserine;
(c) obtaining the phosphatidylserine from said removed upper layer by standard means;
(d) washing the phosphatidylserine obtained in step (c) with an appropriate aqueous solution to remove excess L-serine;
(e) optionally washing the phosphatidylserine obtained in step (d) with a suitable organic solvent, preferably ethanol at an elevated temperature; and
(f) drying the phosphatidylserine obtained in step (e).

In one particular embodiment of the process of the invention, said phospholipase is preferably phospholipase D.

In another embodiment of the process of the invention, said process may further comprise the step of deactivating any residual phospholipase activity in the obtained phosphatidylserine by suitable means.

In yet another preferred embodiment of the process of the invention, said phospholipase is immobilized on an insoluble matrix and is optionally surfactant coated, and, after step (a), the reaction mixture is allowed to stand until the phospholipase precipitates.

In a further aspect the present invention provides a process for preparing a stable phosphatidylserine oil-based liquid preparation of phosphatidylserine, comprising the step of dissolving in a suitable oil base the phosphatidylserine composition of matter of the invention wherein the PS is present in the form of a salt which is substantially soluble in organic solvents, dissolved in an oil, preferably a medium-chain triglyceride. Preferably, said PS dissolved in oil is in the form of a sodium salt. Preferably, said oil base is medium-chain triglycerides or a vegetable oil.

In a last aspect, the present invention provides a process for preparing a stable liquid-based dispersion of phosphatidylserine comprising the step of dispersing the phosphatidylserine composition of matter of the invention wherein the PS is present in the form of a salt which is substantially non-soluble in organic solvents, dissolved in an oil, preferably a medium-chain triglyceride, and wherein preferably said PS dissolved in an oil is in the form of a calcium salt, in a suitable oil base, preferably triglyceride base and particularly medium-chain triglycerides or vegetable oil. It is to be noted that further ingredients may be added to this liquid preparation, in order to enrich the mixture.

The present invention also provides the stable phosphatidylserine composition of matter whenever prepared by any one of the above-described processes.

DETAILED DESCRIPTION OF THE INVENTION

The following abbreviations are employed throughout this specification:
EDTA: ethylenediaminetetraacetic acid
GC: gas chromatography
GPS: de-acylated PS
HPLC: high performance liquid chromatography
HPTLC: high performance thin layer chromatography
LPS: lyso-PS
MCT: medium chain triglycerides
NMR: nuclear magnetic resonance
PA: phosphatidic acid
PC: phosphatidylcholine
PE: phosphatidylethanolamine
PG: phosphatidylglycerol
PI: phosphatidylinositol
PLC: phospholipase C
PLD: phospholipase D
PS: phosphatidylserine
RH: relative humidity
RT: room temperature As mentioned above, phosphatidylserine (PS) is an essential component of cell membranes, which is particularly important in the well-functioning of brain cells, with a known link to memory, mood, cognitive performance and learning ability. For all its important functions, it is desirable to supplement PS in the human diet. Although supplements do exist in the market, they are very problematic with relation to the amount that is de facto delivered to the consumer, since there is an inherent problem of degeneration and decomposition of PS in the compositions currently available to the general population.

PS is generally known to be unstable. Even pure dry powders stored under cold conditions are prone to high rates of degradation. Furthermore, compositions of high concentrations of PS, and pure PS are usually more prone to instability problems. It has been described that pure PS is prone to degradation at the rate of 0.5% w/w per day [Sigma Catalog]. The exact cause or mechanism of this degradation is not fully known. In many cases, hydrolysis or transphosphatidylations reactions are blamed; however, in many cases no products of such reactions can be isolated.

In order to overcome this instability problem, the present inventors have developed and present herein a PS composition which is more stable. Uses and methods of producing such stable PS are also presented. This enhanced stability is provided by various means, especially addressing the several potential causes for PS de-stabilization, which are detailed herein below.

The terms "stabilized" and "stable" are used herein synonymously.

Thus, in a first aspect, the present invention provides a stable PS composition of matter comprising from about 1 to about 99% (w/w) phosphatidylserine.

As already mentioned, the main known causes of PS instability are residual enzyme activity in PS preparations, as well as chemical degradation of PS, like decarboxylation, lipid peroxidation, and hydrolysis of the phospholipids fatty acids.

Therefore, the stable PS composition of matter provided by the invention is devoid or has minimal enzyme activity, it is chemically stable and storage stable. Such attributes are clearly demonstrated in the following Examples.

In one embodiment of the composition of matter of the invention, said composition comprises from about 1 to about 99% (w/w) PS, preferably from about 2.5 to 80% (w/w), from about 1 to about 99% (w/w) other functional ingredients, preferably from about 5 to 90% (w/w), from about 1 to about 99% (w/w) phosphatidylcholine (PC), preferably from about 1 to 25% (w/w), preferably from about 1 to about 99% (w/w) phosphatidylethanolamine (PE), preferably from about 1 to 10% (w/w), from about 0.1 to about 99% (w/w) phosphatidylinositol (PI), preferably from about 0.5 to 10% (w/w), from about 1 to about 99% (w/w) Omega-3 source, preferably from about 10 to 90% (w/w), from about 1 to about 99% (w/w) Omega-6 source, preferably from about 10 to 90% (w/w), and/or from about 1 to about 99% (w/w) sterol or sterol esters, preferably from about 1 to 65% (w/w).

In addition, the composition of matter of the invention is characterized in that its content does not exceed 15% of phosphatidic acid (PA). Preferably, the PA content is below 10%, more preferably between 1 and 7%.

In another embodiment, the composition of matter of the invention is characterized in that no more than about 1 to about 5% of the phosphatidylserine is decomposed after a storage period of at least 6 months, preferably at least 12 months, more preferably at least 24 months.

In other words, at least 95% of the original PS content of the composition of matter of the invention is preserved after a storage period of at least 6 months, preferably at least 12 months, more preferably at least 24 months. Preferably, at least 97% of the original PS content is preserved after said storage period, and more preferably at least 99% of the original PS content is preserved.

In one particular embodiment of the present invention, the composition of matter is substantially devoid of phospholipase activity, particularly phospholipase D activity. By substantially devoid it is meant that less than 1 unit/mL, preferably below 0.1 units/mL or even 0.05 units/mL is the maximum residual enzyme activity that may be found in the composition of matter of the invention. In practical terms, this amount of residual enzymatic activity is so negligible that it is almost at the limit of being measurable, as demonstrated in results shown in Table 3.

The phospholipase D (PLD) (Phosphatidylcholine phosphatidohydrolase, EC 3.1.4.4) used in the production of PS as described can be obtained from animal, microbial, fungal, or plant sources. Examples are cabbage PLD, *Streptomyces* sp. PLD, *Streptomyces chromofuscus*, etc. By using an immobilized PLD preparation the present inventors were able to minimize or even avoid the presence of this enzyme in the final PS product preparation, thus minimizing or avoiding the risk of continuous PS degradation by the process enzyme.

In another particular embodiment, the phosphatidylserine composition of matter of the present invention is in powder form. As demonstrated in Example 1, the PS preparation obtained through the synthesis method employed by the inventors is in powder form.

In a further embodiment, the PS comprised in the composition of matter of the invention is in the form of a salt which is substantially soluble in organic solvents, particularly salts of monovalent ions, preferably sodium salt.

Enzymatically produced phosphatidylserine preparations are usually produced as a salt of divalent metals, most preferably $Ca^{+2}$. These salts are not soluble in many organic solvents, such as oils, hexane, and even alcohols. The divalent salts can be made soluble in organic solvents by utilization of different techniques, ranging from the usage of complex mixtures of solvents, the utilization of different additives and to salt exchange. In the latter the divalent metal ions are exchanged with monovalent metal ions, such as $Na^+$. This is achieved by exposing the PS divalent salts to excess of the monovalent ions under conditions that will favor the exchange. In addition one can use selective metal chelators, such as ethylenediaminetetraacetic acid (EDTA) or EGTA. These chelators shift the equilibrium due to their high association coefficients to the divalent metals, and $Ca^{+2}$ in particular. The chelators scavenge the $Ca^{+2}$ ions in the presence of excess of sodium ions which take their place in the salts of PS. This is carried out in an aqueous environment with 1 to 3 equivalents of the metal chelators at ambient conditions, and optionally at elevated temperatures. The resulting sodium salt is more readily soluble in organic solvents.

By substantially soluble in organic solvents it is meant solutions of PS in the range of 1% w/w to 40% and even 60%, which are feasible and form clear solutions.

Organic solvents are, for example, hexane, petroleum ether, toluene, ethanol, oils and fats (triglycerides), fatty acids ethyl esters, etc.

In an even further embodiment, the PS comprised in the composition of matter of the invention is in the form of a salt which is substantially non-soluble in organic solvents, particularly salts of divalent ions, preferably a calcium salt. Alternatively, it may also be a magnesium salt.

The composition of matter of the invention may further optionally comprise physiologically/pharmaceutically acceptable additives, such as free-flow agents, emulsifiers, stabilizers preservatives, colorants, anti-foaming agents and anti-caking agents, as well as diluents, excipients, and carriers.

In a yet further embodiment, the phosphatidylserine composition of matter of the invention is for use as a dietary supplement, nutraceutical food and/or as a drug additive.

In a second aspect, the present invention provides a stable liquid preparation of phosphatidylserine comprising the phosphatidylserine composition of matter of the invention wherein the PS is present in the form of a salt which is substantially soluble in organic solvents, dissolved in an oil, preferably a medium-chain triglyceride. Preferably, said PS dissolved in an oil is in the form of a sodium salt.

In one first embodiment, the liquid preparation of the invention comprises from about 1 to about 90% (w/w) of phosphatidylserine, preferably from about 2.5 to about 55% (w/w).

In another embodiment, the liquid phosphatidylserine preparation of the invention is characterized in that no more than about 1 to about 5% of the phosphatidylserine is decomposed after a storage period of at least 6 months, preferably at least 12 months, more preferably at least 24 months.

Similarly to the composition of matter of the invention, this means that at least 95% of the original PS content of the liquid PS preparation of the invention is preserved after a storage period of at least 6 months, preferably at least 12 months, more preferably at least 24 months. Preferably, at least 97% of the original PS content is preserved after said storage period, and more preferably at least 99% of the original PS content is preserved.

In a further embodiment, the liquid phosphatidylserine preparation of the invention further comprises additional biofunctional ingredients, preferably at least one of lecithin, phospholipids, vitamins, anti-oxidants, minerals, nutritional proteins or peptides, sterol and other derivatives, nutritional carbohydrates and their derivatives, amino acids, plant extracts, fermentation products, glyceride derivatives (mono- and di-glycerides), poly-unsaturated fatty acids, and Omega-3 and/or Omega-6 lipids In a yet further embodiment, the phosphatidylserine liquid preparation of the invention is for use as a dietary supplement, nutraceutical food and/or drug additive.

In a third aspect, the present invention provides a stable dispersion of phosphatidylserine comprising the stable phosphatidylserine composition of matter of the invention, wherein the PS is present in the form of a salt which is substantially non-soluble in organic solvents, dispersed in a liquid base. Preferably, said salt is a calcium salt. Thus, the stable dispersion of PS is a calcium salt of PS dispersed in a liquid base which is preferably lipid, more preferably an oil base. Alternatively, the stable dispersion of PS is a magnesium salt of PS dispersed in a liquid base which is preferably lipid, more preferably an oil base.

In one embodiment, a lipid base can be oil, esters of fatty acids, free fatty acids and other derivatives.

The dispersions of phosphatidylserine in a lipid or organic carrier are characterized in that this kind of carrier does not enable full solubilization of the PS. Such a carrier can be an edible oil (e.g., triglyceride-based product such as vegetable oil, fish oil, etc.), an organic polymer, carbohydrates and their derivatives, protein and peptide preparations, etc.

The PS which is not soluble in said carrier is found in a crystalline form, at different particle sizes. At this form the PS is less accessible to decomposing factors, such as water, glycerol, residual enzyme, and any other factor which requires reaction on a molecular level with the PS molecule or one of its substituents.

The PS dispersion may also be obtained as a solid or semi-solid (extremely high viscous form) form. The solid nature further inhibits or delays any chemical or enzymatic degradation processes that might result in the reduction of levels of the PS active ingredient, merely due to the fact that the kinetic profile of such processes in solid phase have substantially lower rate coefficients.

Alternatively, the liquid base is not lipid, and may be organic or inorganic liquid polymers, liquid carbohydrates, etc.

Preferably, said phosphatidylserine dispersion of the invention comprises from about 1 to about 70% (w/w) phosphatidylserine, most preferably from about 5 to 45% (w/w).

The inventors have produced a PS dispersion or a fluid PS containing 40% of PS, as shown in the Examples.

A common product for dietary supplements is a fluid PS in MCT oil with 20% w/w of PS. This allows the production of 500 mg softgel capsules with 100 mg PS, the standard and most common daily serving of PS currently available in the market. For softgel encapsulation, which is one of the most popular forms of capsules today, one must have a fluid preparation at ambient conditions or at temperatures not exceeding 35° C. These limitations arise from the softgel encapsulation technique and machinery. Until now, it had not been possible to produce fluid PS with over 20% of PS content. It seems advantageous to produce fluid PS with higher concentrations of PS, since it will allow smaller capsule sizes or the addition of other ingredients to the capsule, without the need to enlarge the capsule or to increase the number of daily capsules a person needs to ingest. This is advantageous both from the economic point of view, as for being more palatable for the customer.

The present inventors have developed a fluid PS which has such advantages, without compromising on its stability. In the present invention PS sodium salt is solubilized in hexane and added to an oil carrier, preferably MCT. PC or lecithin is not added and the amount of MCT used is changed resulting in a much more concentrated form of PS. This concentration is above the solubility of PS sodium salt in MCT and hence, part of the PS precipitates. Consequently, the PS in the formulation obtained is partly soluble and partly dispersed, enabling fluid properties, easy handling and dosing, as well as high stability.

In one preferred embodiment of the phosphatidylserine dispersion of the invention, said oil base is a triglyceride base, particularly medium-chain triglycerides base or vegetable oil.

In another embodiment, the phosphatidylserine dispersion of the invention further comprises additional bio-functional ingredients, preferably at least one of lecithin, phospholipids, vitamins, anti-oxidants, minerals, nutritional proteins or peptides, sterol and other derivatives, nutritional carbohydrates and their derivatives, amino acids, plant extracts, fermentation products, glyceride derivatives (mono- and di-glycerides), poly-unsaturated fatty acids, and Omega-3 and/or Omega-6 lipids In a further embodiment, said phosphatidylserine dispersion of the invention is for use as a dietary supplement, nutraceutical food and/or drug additive.

In another aspect, the present invention provides a food article comprising PS in any one of the forms provided by the invention, i.e., as a phosphatidylserine composition of matter, as a PS liquid preparation or as a PS dispersion.

In one embodiment, said food article optionally further comprises at least one additional bio-functional ingredient, for example a bio-functional ingredient as described above.

In a following aspect, the present invention provides a pharmaceutical composition comprising as active agent PS in any one of the forms provided by the invention, i.e., as a phosphatidylserine composition of matter, as a PS liquid preparation or as a PS dispersion, and optionally further comprising at least one additional active agent and/or at least one pharmaceutically acceptable additive, diluent, carrier or excipient. The pharmaceutical composition of the invention may comprise additional pharmaceutically active agents.

The preparation of pharmaceutical compositions is well known in the art and has been described in many articles and textbooks, see e.g., Remington's Pharmaceutical Sciences, Gennaro A. R. ed., Mack Publishing Company, Easton, Pa., 1990, and especially pages 1521-1712 therein.

The pharmaceutical compositions of the invention can be prepared in dosage units forms. The dosage forms may also include sustained release devices. The compositions may be prepared by any of the methods well known in the art of pharmacy. Such dosage forms encompass physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG.

Oral administration is the preferred route to deliver the pharmaceutical composition of the invention, although other routes may also be feasible.

The pharmaceutical composition may be administered to a subject in need, in a single or multiple occasions. The "effective treatment amount" of the composition of the invention is determined by the severity of the condition in conjunction with the therapeutic objectives, the route of administration and the patient's general condition (age, sex, weight and other considerations known to the attending physician). Accordingly, it will be necessary for the therapist to titer the dosage and modify the route of administration as required to obtain the optimal therapeutic effect.

In yet another aspect, the present invention provides a capsule containing PS in any one of the forms provided by the invention, i.e., as a phosphatidylserine composition of matter, as a PS liquid preparation or as a PS dispersion. Said capsule is preferably a soft gelatin capsule.

As mentioned above, PS has been correlated with the improvement of mood and memory, as well as cognitive performance and learning ability.

Therefore, the present invention also provides the use of any of the PS preparations described in the invention, i.e., as a phosphatidylserine composition of matter, as a PS liquid preparation or as a PS dispersion, as an enhancer of cognitive performance and learning ability.

It is a subsequent aspect of the present invention to provide PS, in any one of the forms provided by the invention, i.e., as a phosphatidylserine composition of matter, as a PS liquid preparation or as a PS dispersion, for use in preventing memory loss, particularly age-related memory loss.

In a further aspect, the present invention provides a process for the preparation of a stable phosphatidylserine composition of matter, comprising the steps of:

(a) incubating an aqueous mixture of L-serine and optionally appropriate organic solvents with lecithin in the presence of an immobilized phospholipase for a suitable period of time to give phosphatidylserine;
(b) removing the upper layer which contains the phosphatidylserine;
(c) obtaining the phosphatidylserine from said removed upper layer by standard means;
(d) washing the phosphatidylserine obtained in step (c) with an appropriate aqueous solution to remove excess L-serine;
(e) optionally washing the phosphatidylserine obtained in step (d) with a suitable organic solvent, preferably ethanol at an elevated temperature; and
(f) drying the phosphatidylserine obtained in step (e).

In one particular embodiment of the process of the invention, said phospholipase is preferably phospholipase D.

In another embodiment of the process of the invention, said process may further comprise the step of deactivating any residual phospholipase activity in the obtained phosphatidylserine by suitable means.

Said suitable means may be (a) EDTA treatment, (b) further incubation with organic solvents, preferably methanol, ethanol or propanol, (c) thermal deactivation, and/or (d) addition of PLD inhibitors.

In yet another preferred embodiment of the process of the invention, said phospholipase is immobilized on an insoluble matrix and is optionally surfactant coated, and, after step (a), the reaction mixture is allowed to stand until the phospholipase precipitates.

The immobilized PLD preparations may be used when the process is carried out in organic or in aqueous media, or in mixtures thereof, also known as biphasic systems.

In step (a) of the above-described process, the lecithin is added to an aqueous solution of L-serine, optionally in the presence of suitable organic solvents that assist in the dispersion and/or solubilization of the lecithin raw material in the reaction mixture. The mixture is preferably stirred for a suitable period of time, preferably about 1 hour, in order to homogeneously disperse the phospholipids in the reaction media.

The enzymatic reaction itself is carried out for a suitable period of time, preferably at least 12 hours, whilst stirring, and the reaction mixture is then allowed to stand.

The upper layer of the reaction, containing the phospholipids fraction, is obtained by standard techniques, like for example centrifugation, filtration, pressure filtration, decantation, etc. The resulting phosphatidylserine is further washed with an appropriate aqueous solution, to remove any excess L-serine, and dried, in order to obtain phosphatidylserine which is substantially devoid of phospholipase activity.

Where immobilized PLD preparations were used in the production of PS, either powder or fluid formulations, the final PS formulations exhibited superior stability in comparison to commercially available PS formulations, as evidenced by minimal residual enzymatic activity. Enzyme leakage from immobilized preparation is a highly common phenomenon, due to mechanical degradation of the matrix or insufficient immobilization. In order to avoid this problem, the inventors have employed further steps to deactivate any enzyme activity present in the final PS. These further steps include: (i) enzyme deactivation via incubation with organic solvents, preferably methanol, ethanol or propanol, or any other organic solvent that is capable of inactivating the enzyme, at elevated temperatures (up to 120° C.); (ii) thermal deactivation; (iii) addition of additives that inactivate the enzyme, like for example EDTA treatment; (iv) addition of PLD inhibitors.

Treatment of the PS preparation with enzyme inhibitors or with selective reagents that remove enzymatic co-factors, such as $Ca^{+2}$ ions, is preferably carried out in aqueous medium to ensure the accessibility of such inhibitors or reagents to the residual enzyme or water-soluble co-factors.

Treatment with selective metal-ion chelators, such as, but not restricted to, ethylenediaminetetraacetic acid (EDTA) and its corresponding salts and derivatives results in selectively binding of $Ca^{+2}$ ions, making them inaccessible to any residual enzyme. Thus, even if residual enzyme is present in the preparation it will not be able to exert any transphosphatidylation or hydrolytic activity due to lack of the essential co-factor.

The PS preparation treated with an appropriate EDTA salt is further washed with fresh aqueous solutions and obtained by filtration and subsequent drying. Preferably, the PS preparation is obtained by extraction to an organic media. Said organic media can be composed of organic solvent or a mixture of organic solvent or a lipid system, such as oil, ethyl esters of fatty acids, free fatty acids, partially hydrolyzed triglycerides, etc. Additionally, said organic media can contain both organic solvent and lipid carrier at different ratios. Commonly MCTs are used as a lipid carrier. In case an organic solvent, such as a hydrocarbon organic solvent, is used in the extraction of the treated PS preparation, said solvent is further removed by standard techniques.

In a further aspect the present invention provides a process for preparing a stable phosphatidylserine oil-based liquid preparation of phosphatidylserine, comprising the step of dissolving in a suitable oil base the phosphatidylserine composition of matter of the invention wherein the PS is present in the form of a salt which is substantially soluble in organic solvents, dissolved in an oil, preferably a medium-chain triglyceride. Preferably, said PS dissolved in an oil is in the form of a sodium salt. Preferably, said oil base is medium-chain triglycerides or a vegetable oil.

In a last aspect, the present invention provides a process for preparing a stable liquid-based dispersion of phosphatidylserine comprising the step of dispersing the phosphatidylserine composition of matter of the invention wherein the PS is present in the form of a salt which is substantially non-soluble in organic solvents, dissolved in an oil, preferably a medium-chain triglyceride, and wherein preferably said PS dissolved in an oil is in the form of a calcium salt, in a suitable oil base, preferably triglyceride base and particularly medium-chain triglycerides or vegetable oil. It is to be noted that further ingredients may be added to this liquid preparation, in order to enrich the mixture. For example, phosphatidylcholine content may be increased by adding more lecithin.

Thus, the PS produced by the processes of the invention is obtained as either a stabilized powder form or as a stabilized oil-based liquid preparation of phosphatidylserine, both being substantially devoid of phospholipase activity.

The present invention also provides the stable phosphatidylserine composition of matter whenever prepared by any one of the above-described processes.

In sum, several mechanisms, known and unknown, are believed to be the cause of PS degradation. Among the known mechanisms, the following may be highlighted: (1) enzymatic hydrolysis and transphosphatidylation, yielding PA or PG; (2) partial or full hydrolysis of the phospholipid fatty acids, yielding lyso-PS or de-acylated-PS (GPS) correspondingly; (3) removal of the phosphate group, yielding diglycerides (DAG); (4) decarboxylation of L-serine carboxylate group to yield PE or other more complex products; (5) phospholipids hydroperoxidation; and (6) oxidation of the primary amine group of the L-Serine head-group, caused by air, light, etc.

With regards to amines, and primary amines in particular, are highly sensitive to oxidation. The products of such oxidation are numerous and their identification is almost impossible. Therefore, stabilized PS which is able to withstand amine-oxidation was produced by the incorporation of additives characterized in their ability to protect sensitive chemical groups from oxidation. These additives, possessing anti-oxidative traits were added to powder PS as well as to fluid PS, and especially to fluid PS encapsulated in softgel capsules. The latter are extremely prone to PS degradation. The antioxidants used consisted of Rosemary extract, Tocopherols and Ascorbyl palmitate at levels of 0-5000 ppm, and BHA, BHT and TBHQ at levels of 0-200 ppm. Other antioxidants or blends of antioxidants, either synthetic or natural, are incorporated in this invention. The levels of antioxidants used to protect the PS from degradation are at least 100 ppm, and preferably 1000-3000 ppm. These capsules, as well as their bulk material, were analyzed at room temperature and at accelerated tests for their stability. The bulk material was stored in a sealed container in a dark place at room temperature.

In sum, the stabilized PS preparations of this invention were shown to be particularly stable in terms of enzymatic degradation, achieved by the use of immobilized bio-catalysts, residual enzyme de-activation, and the use of enzymatic inhibitors.

The stability of the PS generated by the methods described herein was analyzed through monitoring the different degradation products of each degradation route, as listed above. The presence of these products was measured by $^{31}$P-NMR, and common chromatography methods (HPTLC, HPLC-ELSD, and GC). In all cases no elevation in the presence of such degradation markers was detected, leading to the conclusion that none of these degradation pathways was able to take place, yielding a highly stable PS.

Therefore, the present invention provides preparations of stable phosphatidylserine in any one of three forms, composition of matter, liquid or dispersion, which are resistant to degradation by at least one of the following routes: enzymatic hydrolysis and transphosphatidylation, partial or full hydrolysis of the phospholipid fatty acids, removal of the phosphate group, decarboxylation of L-serine carboxylate group, phospholipids hydroperoxidation, oxidation of the primary amine group of the L-Serine head-group.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Example 1

Preparation of Stable Phosphatidylserine in Powder Form Using an Immobilized Enzyme Preparation 1. Preparation of the Immobilized Enzyme In this invention the inventors have utilized several commercially available PLDs, such as Phospholipase D from *Streptomyces* sp., cabbage, and *Streptomyces chromofuscus*. In all cases, these enzymes exhibited high reactivity and high quality PS was synthesized. Most importantly, the levels of phosphatidic acid were usually low (data not shown).

Several PLDs were immobilized by different techniques and using different insoluble matrices as carriers. Matrix-immobilized, preferably surfactant-coated, phospholipase was prepared according to the methods described in WO00/56869, fully incorporated herein by reference. Commercially available insoluble matrices, designed for enzymatic covalent immobilization, were also used, such as Eupergit epoxy activated matrices (Rohm and Haas, Germany).

In short, crude PLD enzyme (300 mg/l protein) was dissolved in 1 L Tris buffer pH 6.5, containing 4 g of insoluble inorganic or organic matrix (Celite, silica gel, alumina or polypropylene). The solution was stirred vigorously with a magnetic stirrer for 30 minutes at 25° C. For surfactant-coated immobilized enzyme preparations, a non-ionic surfactant was added drop-wise to the stirred enzyme solution. Both surfactant-coated immobilized phospholipases and immobilized-crude phospholipases were sonicated for 10 minutes and then stirred for 8 hours at 25° C. The resulting precipitate was collected by filtration or centrifugation (12,000 rpm, 4° C.), followed by overnight freezing at −20° C. and lyophilization.

As shown in Table 1, these PLD immobilized preparations successfully produced phosphatidylserine by transphosphatidylation of lecithin with L-serine. D-serine may also be used for these preparations. PS yield was always over 30%. Different grades of PS can be produced depending on the lecithin starting material. Most importantly, the immobilized PLD preparations exhibited high activity irrespective of the lecithin starting material employed in the process (data not shown).

2. Stable PS Preparation 250 g of L-serine (Rexim, France) were placed in a 1 Liter reactor filled with 750 ml of appropriate buffer (pH 3.5-7), for example citrate buffer, containing 200 mM $CaCl_2$. After complete dissolution of the serine, 53 g of fractionated soy lecithin (Solae Company, USA) were added, optionally with other organic solvents, such as hexane, ethyl acetate, diethyl ether, etc., to assist in the dispersion of the phospholipids. The mixture was stirred at temperatures of 20-60° C. for 0.5-2 hours, to homogeneously disperse the phospholipid in the reaction medium. 1.25 g of enzymatic preparation (Reaction 2, PLD2, Table 1) was added to the reaction media. The reaction mixture was stirred for 24 hours and then left without stirring until the enzymatic preparation precipitated to the bottom of the reactor. The upper layer, containing the phospholipid fraction, was removed from the reactor. The phosphatidylserine was obtained from this fraction and washed with appropriate aqueous solutions to remove excess serine. The phosphatidylserine obtained was practically free of enzyme traces, mainly due to the fact that the enzyme was immobilized.

From this preparation, 47 g of phosphatidylserine were obtained with over 30% purity. This procedure was repeated with the enzymatic preparations shown in Table 1 (1, 2, 3 and 4, respectively). Yields were as indicated for the $1^{st}$ Batch. The immobilized enzymatic preparations were re-used in further batches ($2^{nd}$, $3^{rd}$, and $4^{th}$, respectively) and the results obtained are also summarized in Table 1.

TABLE 1

Immobilized PLD preparations, reaction conditions and PS yield

| Reaction | Enzyme | Matrix | Reaction Temperature (° C.) | % PS in every batch $1^{st}$ | $2^{nd}$ | $3^{rd}$ | $4^{th}$ |
|---|---|---|---|---|---|---|---|
| 1 | PLD1 | Eupergit 1014F | 42 | 31 | 61 | | |
| 2 | PLD2 | Duolite A568 | 42 | 39 | 45 | 47 | 43 |
| 3 | PLD1 | Duolite A568 | 42 | 46 | 45 | 44 | 55 |
| 4 | PLD1 | Duolite A568 | 37 | 39 | 44 | 43 | 44 |

Example 2

Enzyme Deactivation

A. Organic Solvents

In order to deactivate any residual enzyme that may have leaked from the soluble matrix, the PS obtained as described in Example 1 was vigorously agitated in the presence of a deactivating organic solvent, preferably methanol or ethanol, at temperatures ranging from 20° C. to 120° C., for appropriate periods of time, ranging from 0.5 to 10 hours.

The organic solvent can dissolve the PS, ensuring full access of the solvent to any residual enzyme found in the PS. The selected organic solvent does not fully dissolve the PS, and thus creates a trituration-like process, enabling the solvent to dissolve only small amounts of the PS, which ensures the deactivation of any residual enzyme. Under these conditions, after the completion of the deactivation process, the PS was filtered and dried. When the organic solvent used in the deactivation dissolved significant amounts of PS, the PS was obtained after the completion of the deactivation treatment by standard techniques such as solvent removal and drying, optionally with spray drying. These treatments significantly reduced the decomposition of both powder and liquid PS preparations. For powder PS, the initial PS concentration was about 22%, and no significant change was observed after 4 months of storage. For liquid PS, the initial PS concentration was about 22.67%, and again no significant change (a 0.02% decrease) was observed after 4 months of storage.

Table 2 describes the decrease in the enzymatic activity as a function of the time of deactivation, after organic solvent (ethanol) deactivation with heating.

TABLE 2

Organic solvent deactivation with heating

| Duration of heating (80° C.) in hours | Enzyme residual activity (Units/ml) |
|---|---|
| 1 | 0.0458 |
| 2 | 0.0248 |
| 4 | 0.0088 |
| 4.5 | 0.0082 |
| 5 | 0.0067 |

Table 3 describes three PS batches prepared by the inventors, showing extremely low residual enzymatic activity.

TABLE 3

Comparison between three PS preparations

| PS Preparation Number | Residual enzymatic activity in Enzymotec's preparations (units/ml)* |
|---|---|
| 1 | 0.0054 |
| 2 | 0.0058 |
| 3 | 0.0042 |

*Limit of detection of the method: 0.002 –0.003 units/ml.

Next, the inventors analyzed other PS preparations produced by different PS manufacturers. The inventors found that the residual enzymatic activity of PLD was considerably higher comparing to the residual enzymatic activity of PS prepared by the inventors. For example, one such "foreign" PS preparation exhibited 0.0242 and 0.0196 units/ml in two batches of similar grade PS preparations.

B. Enzyme Deactivation Through EDTA—Preparation of Stable Liquid Phosphatidylserine The powder PS obtained in Example 1 was dispersed in a 0.2M EDTA solution of 1:1 water:ethanol mixture, and stirred for 10 hours at 25° C. Next, the phosphatidylserine was extracted with 250 ml of n-hexane. The n-hexane layer was washed twice with water. MCT (95 g) was added to the n-hexane solution and after evaporation of the n-hexane, a clear oily fluid of phosphatidylserine formulation was obtained.

Powder PS is obtained by the process of Example 1 as a calcium salt, which is not soluble in organic solvents. Treatment with EDTA plays a dual role in this PS. In one hand, it renders the PS soluble in organic solvents, by scavenging the $Ca^{+2}$ ions, which are substituted by $Na^+$, consequently making PS soluble, and thus the liquid form is obtained. At the same time, since $Ca^{+2}$ is the co-factor for PLD catalytic activity, $Ca^{+2}$ depletion results in inactivation of residual enzyme.

The PS preparation treated with the appropriate EDTA salt was further washed with fresh aqueous solutions and the PS obtained by filtration and subsequent drying.

The resulting PS can be obtained as either a stabilized powder form or as a stabilized oil-based liquid preparation of phosphatidylserine, both are substantially devoid of phospholipase activity.

The fluid PS, treated with EDTA, was kept in a sealed container in a cool and dark place. PS concentration was analyzed through HPLC with ELS detector, and through $^{31}P$-NMR.

Table 4 shows the PS concentration as measured soon after its manufacture and after 4 months of monitored storage.

TABLE 4

PS stability after EDTA treatment (post-organic solvent treatment)

| Product Description | Duration of Storage | PS concentration when Manufactured (%) | PS concentration after storage (%) |
|---|---|---|---|
| Fluid PS | 4 months | 22.67 | 22.65 |

Example 3

Determination of Phospholipase D Activity

Phospholipase D activity was assayed by spectrophotometry using a modified method reported by S. Kato et al. [Kato, S. et al. (1984) *Agric. Biol. Chem.*, 48, 2181-2188].

(1) Definition of Enzyme Unit

One enzyme unit of phospholipase D is defined as the amount of an enzyme which liberates one micro mole of Choline in a minute from the substrate under the conditions specified below.

(2) Reagents
1. 5% Soybean lecithin (Epikuron 200, phosphatidylcholine 95%) emulsion
2. 5% Phosphatidylserine preparation emulsion
3. 0.1 mol/l Tris-maleate-NaOH buffer, pH 5.5
4. 0.1 mol/l Calcium chloride solution
5. 7.5% Triton X-100 solution
6. 0.05 mol/l EDTA in 1 mol/l Tris-HCl buffer, pH 8.0
7. Coloring Reagent: 3 units of Cholineoxidase (from *Alcaligenes* sp.), 6 units of peroxidase (from Horseradish), 1 mg of phenol and 0.6 mg of 4-amino-antipyrine in 4 ml of 50 m mol/l Hepes-NaOH buffer (pH 7.4).
8. 1.43 μmole/ml (0.2 g/l) Choline chloride standard solution
9. 0.01% enzyme solution (3) Procedure The following solutions were prepared:

Solution A: In a test tube, 0.1 ml of 5% Soybean lecithin emulsion and 5% Phosphatidylserine emulsion, 0.1 ml of 0.1 mol/l Tris-maleate-NaOH buffer (pH 5.5), 0.05 ml of 0.1 mol/l calcium chloride solution and 0.15 ml of 7.5% Triton X-100 solution were mixed well and incubated for 5 min. in a water bath at 37° C. To this solution, 0.1 ml of enzyme solution was added, and exactly after 10 minutes, 0.2 ml of EDTA solution was added and the incubating tube placed in boiling water for 5 min. The tube was then removed and cooled to room temperature.

Solution B: In a test tube, 0.1 ml of 5% Phosphatidylserine emulsion, 0.1 ml of 0.1 mol/l Tris-maleate-NaOH buffer (pH 5.5), 0.05 ml of 0.1 mol/l Calcium chloride solution and 0.15 ml of 7.5% Triton X-100 solution were mixed well and incubated for 5 min. in a water bath at 37° C. 0.1 ml of enzyme solution was added to this solution, and exactly after 10 minutes of incubation, 0.2 ml of EDTA solution was added and the tube placed in boiling water for 5 minutes. The tube was then removed and cooled to room temperature.

Blank solution: Distilled water

Standard solution—Choline chloride standard solution respectively instead of the enzyme solution.

4 ml of coloring reagent was then added to each of the four solutions, mixed well and incubated for 20 minutes at 37° C. Optical density of the reaction, as well as of the standard solutions, was read at 500 nm (light path 1 cm) against the blank solution.

(4) Enzyme Unit Calculation

Phospholipase D activity (unit per ml)=($\Delta E$ of Solution A−$\Delta E$ of solution B)/$\Delta E$ of standard X 0.143. $\Delta E$: optical density at 500 nm against blank solution.

Example 4

Preparation of Stable Phosphatidylserine in Powder Form Using Non-Immobilized Enzyme and Enzyme Deactivation 250 g of L-serine were placed in a 1 Liter reactor filled with 750 ml of appropriate buffer (pH 3.5-7), like citrate buffer for example, containing 200 mM $CaCl_2$. After complete dissolution of the serine, 53 g of fractionated soy lecithin were added, optionally with other organic solvents to assist in the dispersion of the phospholipids. The mixture was stirred at temperatures of 20-60° C. for 0.5-2 hours, to homogeneously disperse the phospholipid in the reaction media. 1.25 g of enzyme (PLD) was added to the reaction media. The reaction mixture was stirred for 24 hours. The upper layer containing the phospholipids was removed from the reactor. The phosphatidylserine was obtained from this layer and then washed with aqueous solutions. The phosphatidylserine was further treated with an organic solvent, preferably methanol or ethanol, under elevated temperatures for at least 0.5 hours, to deactivate any traces of enzyme. The phosphatidylserine was obtained by filtration or solvent removal and dried. The final phospholipid fraction yield was 47 g, of which over 60% consisted of PS. The PS produced was also used in the production of fluid preparation (see below). Both fluid and powder preparations were analyzed for product stability.

After enzyme deactivation, fluid (dissolved in MCT) and powder PS were kept in sealed containers in a cool and dark place. The PS concentration was analyzed using HPLC equipped with ELS detector, and also through $^{31}$P-NMR pre- and post-storage. After 7 (for fluid PS) or 7.5 months (for powder PS) of storage, practically no (or less than 1%) degradation occurred following the de-activation treatment (through organic solvent and elevated temperature).

Example 5

PS Dispersions

Stabilized PS dispersions were prepared by dispersing the stabilized phosphatidylserine (preferably substantially devoid of phospholipase activity), in a suitable oil base, preferably triglyceride base and particularly medium-chain triglycerides (such as MCT or fish oil ethyl esters) or vegetable oil at a temperature of from room temperature up to 80° C., and resulted in a stabilized oil-based PS dispersion. The dispersion was achieved by vigorous stirring, homogenization, pressure-homogenization, and other industrial blending methods.

These formulations were checked for the stability of the phosphatidylserine as a bulk active ingredient and in softgel capsules.

—Preparation of Soft Get Capsules

Dispersed PS was prepared as described above and used in the manufacturing of softgel capsules, which were prepared by routine method for softgel capsules preparation. The capsules containing dispersed PS were stored at three different conditions: (1) in sealed containers in a dark place at room temperature; (2) in sealed containers at 35° C. and 60% RH (accelerated conditions); and (3) in open containers at 35° C. and 60% RH (accelerated conditions). The capsules stored at room temperature (condition 1) were tested for their PS concentration at the end of the manufacturing process and after a storage period of 4 weeks. The capsules stored at accelerated conditions (2 and 3) were tested for their PS concentration at the end of the manufacturing process and after storage periods of 1, 2, 3 and 4 weeks The PS concentration was analyzed using HPLC with ELS detector and/or HPTLC, and through $^{31}$P-NMR. Table 5 shows the PS concentration in the different capsules.

TABLE 5

PS stability in softgel capsules containing dispersed PS preparations

| Sample and storage condition | Pre-Storage PS Concentration* | Post-Storage PS concentration* | | | |
|---|---|---|---|---|---|
| | | 1 wk | 2 wks | 3 wks | 1 mo. |
| Dispersion capsules at RT | 13.26 | n.d | n.d | n.d | 13.15 |
| Dispersion capsules at accelerated conditions in a sealed container | 13.26 | 13.04 | n.d | n.d | 13.28 |
| Non-stabilized fluid capsules at RT | 18.67 | n.d | n.d | n.d | 17.56 |
| Non-stabilized fluid capsules at accelerated conditions in a close container | 18.67 | 17.87 | n.d | 17.04 | 15.07 |
| Non-stabilized fluid capsules at accelerated conditions in an open container | 18.67 | n.d | 17.9 | 17.3 | n.d |

*PS concentrations are in %. Abbreviations: n.d., not done; wk., week, mo., month.

In addition to PS concentration, the content of water and glycerol were also tested in the capsule at the end of manufacture. As mentioned above, water and glycerol, absorbed by the content of the capsule, may promote the degradation of PS. The water content was tested by a standard Karl-Fischer method. The glycerol content was tested by titration according to a standard AOCS (American Oil Chemists Society) method. Table 6 shows the water and glycerol content in capsules manufactured from dispersion and capsules manufactured from fluid PS.

TABLE 6

Water and glycerol content in capsules manufactured from dispersion or fluid PS

| Sample (capsule from) | Water content (%) | Glycerol content (%) |
|---|---|---|
| Dispersion PS | 0.5 | 0.12 |
| Fluid PS | 1.7 | 1.43 |

It can be seen that indeed the dispersion preparations were also effective in minimizing the migration and absorption of water and glycerol buy the PS content of the capsule. This, in addition to other means described above, yields a stabilized PS in the capsule.

Example 6

Other Solid Phase PS

Stabilized phosphatidylserine is also provided by creating PS preparations that are fluid only at elevated temperatures and are solid at room temperature. In this way all degradation reactions are inhibited.

This was achieved by different means:
(a) using different salts of PS, such as calcium or sodium salt creating semi-dispersion;
(b) using edible oils that are solid at room temperature and fluid enough at elevated temperatures to enable the encapsulation process; or
(c) using different hardening additives.

The phosphatidylserine preparation obtained in the above examples (2 g) was mixed with phosphatidylserine that was treated with the EDTA solution and washed with n-hexane (80 g) as described above. Soy lecithin (12.26 g) and PKO (26.45 g) were added to the solution. The n-hexane was evaporated at 45° C. The final material is a turbid oil that is fluid at 45° C. and solid at room temperature.

Example 7

Stabilizing Additives/Antioxidants/Photo-Sensitizers

As mentioned above, several mechanisms or phenomena are believed to be the cause of PS degradation, amongst which are:
1. Enzymatic hydrolysis and transphosphatidylation, yielding PA or PG;
2. Partial or full hydrolysis of the phospholipid fatty acids, yielding lyso-PS or de-acylated-PS (GPS) correspondingly;
3. Removal of the phosphate group, yielding diglycerides (DAG);
4. Decarboxylation of the L-serine's carboxylate group to yield PE or other more complex products;
5. Hydroperoxidation of the phospholipids;
6. Oxidation of the primary amine group of the L-Serine head-group (by air, light, etc.)
  —Degradation Resulting in Lyso-PS, DAG and PE For example, a softgel capsule containing the stabilized PS produced by the method of the invention was analyzed for different degradation markers after 4 months of storage at ambient conditions (i.e., room temperature and uncontrolled humidity). Levels of lyso-PS (0.68 w/w %), DAG (0.35 w/w %) and PE (0.79 w/w %) were negligible, indicating that none of the degradation pathways leading to such by-products took place.
  —Degradation Resulting in PA and PG By-Products The above mentioned analytical methods were also used to verify the stability of the PS preparations produced by the method of the invention in terms of enzymatic degradation. This degradation route is supposed to yield by-products such as PA and PG. After 4 months of storage at ambient conditions levels of PA and PG were identical to pre-storage levels (following PS production), at 2.58 and 0.2 w/w %, respectively. Since no increase in these products was detected, it could be concluded that the PS of the invention is indeed devoid of any enzymatic activity that may lead to its decomposition.
  —Hydroperoxidation Another cause of low-grade products is hydroperoxidation of lipids, which leads to decomposition of sensitive compounds such as PS. This oxidation is highly dependant on the method of material production and treatments that the material has undergone. The main indication of this oxidation is a value called Peroxide Value (PV) which is commonly measured titrimetrically as the equivalents of peroxides in a sample of the material.

The PS preparations of the invention were thoroughly analyzed for their initial as well as developing peroxide values. This analysis was performed on two PS preparations: those treated for enzyme deactivation and optionally treated with enzyme inhibitors, such as EDTA; as well as those preparations produced using immobilized enzymes. The results shown below (Table 7) demonstrate the high stability of the PS of the invention in terms of oxidative stability, as a result of the method of producing PS and subsequent enzyme de-activation treatments.

TABLE 7

PS Oxidative stability

| Sample | Pre-storage PV (meqO$_2$/Kg) | Storage time | Post-storage PV (meqO$_2$/Kg) |
|---|---|---|---|
| Capsule from fluid PS | 0 | 42 | 0 |
| Fluid PS | 0 | 296 days | 0.58 |
| Powder PS | 2.16 | 178 days | 2.18 |

It can be seen that following the production method described in this invention and the various subsequent treatments, no increase in Peroxide Values was detected, confirming the stability of the PS preparations of the invention with respect to hydroperoxidation.

The invention claimed is:

1. A phosphatidylserine (PS) composition of matter for use as a dietary supplement, nutraceutical food and/or drug additive comprising an edible oil base and from about 1 to about 45% (w/w) PS, wherein said PS is in powder form of its salt with a divalent ion, said PS being insoluble in said oil base and being dispersed in said oil base, said composition exhibiting a stability of less than about 5% decomposition of the PS after a storage period of at least 6 months, wherein said PS in powder form of its salt with a divalent ion having been prepared enzymatically by reacting serine with non-solubilized lecithin in an aqueous system in the presence of a phospholipase.

2. The phosphatidylserine (PS) composition of matter of claim 1, wherein said non-solubilized lecithin is dispersed in said aqueous system.

3. The composition of matter of claim 1, comprising as additional ingredients from about 1 to about 99% (w/w) phosphatidylcholine (PC), from about 1 to about 99% (w/w) phosphatidylethanolamine (PE), from about 1 to about 99% (w/w) phosphatidylinositol (PI), from about 1 to about 99% (w/w) polyunsaturated fatty acids, and/or from about 1 to about 99% (w/w) sterol or sterol esters.

4. The phosphatidylserine composition of matter of claim 1, wherein said salt is one of calcium PS salt and magnesium PS salt.

5. The phosphatidylserine composition of matter of claim 1, wherein said edible oil base is an edible triglyceride base.

6. The combination of a capsule and the phosphatidylserine composition of matter of claim 1 contained in said capsule.

7. A method of enhancing cognitive performance and learning ability in a subject, the method comprising administering to said subject an effective amount of the PS composition of matter of claim 1.

8. A method of improving age-related memory loss in a subject, comprising administering to said subject an effective amount of the phosphatidylserine composition of matter of claim 1.

9. The phosphatidylserine composition of matter of claim 5, wherein said triglyceride base is a medium-chain triglyceride oil.

10. The combination of claim 6, wherein said capsule is a soft gel capsule.

11. The composition of matter of claim 3 further including as additional ingredients at least one additional active ingredient selected from the group consisting of lecithin, phospholipids, vitamins, anti-oxidants, minerals, sterols, nutritional carbohydrates, amino acids and poly-unsaturated fatty acids, the total amount of said additional ingredients being 1-99% (w/w).

12. The composition of matter of claim 11, further including additional ingredients at least one pharmaceutically acceptable additive, diluent, carrier or excipient.

* * * * *